US00PP10848P

United States Patent [19]

VandenBerg

[11] Patent Number: Plant 10,848

[45] Date of Patent: Apr. 6, 1999

[54] CHRYSANTHEMUM PLANT NAMED 'CONNIE'

[75] Inventor: Cornelis P. VandenBerg, Salinas, Calif.

[73] Assignee: Yoder Brothers, Inc., Barberton, Ohio

[21] Appl. No.: 990,233

[22] Filed: Dec. 15, 1997

[51] Int. Cl.[6] ..... A01H 5/00

[52] U.S. Cl. ..... Plt./74.1

[58] Field of Search ..... Plt./74.1

*Primary Examiner*—Howard J. Locker

*Attorney, Agent, or Firm*—C. A. Whealy

[57] ABSTRACT

A distinct cultivar of Chrysanthemum plant named 'Connie', characterized by its uniformly mounded plant habit; daisy spoon-type inflorescences that are about 6.2 cm in diameter; attractive bi-colored inflorescences with lavender-tipped ray florets that are white at the base; numerous inflorescences per plant; and excellent garden performance.

1 Drawing Sheet

The present invention relates to a new and distinct cultivar of Chrysanthemum plant, botanically known as *Dendranthema grandiflora* and referred to by the cultivar name Connie.

The new cultivar is a product of a planned breeding program conducted by the inventor in Salinas, Calif. The objective of the breeding program is to create new garden-type Chrysanthemum cultivars having inflorescences with desirable inflorescence forms and floret colors and good garden performance.

The new cultivar originated from a cross made by the inventor in September, 1991, of the *Dendranthema grandiflora* cultivar Christine (U.S. Plant Pat. No. 8,988) as the female, or seed, parent with an unidentified proprietary seedling selection as the male, or pollen, parent.

The cultivar Connie was discovered and selected by the inventor as a flowering plant within the progeny of the stated cross in a controlled environment in Salinas, Calif., in September, 1992. The selection of this plant was based on its desirable inflorescence form and floret colors and excellent garden performance.

Asexual reproduction of the new cultivar by terminal cuttings taken in a controlled environment in Salinas, Calif., has shown that the unique features of this new Chrysanthemum are stable and reproduced true to type in successive generations.

The cultivar Connie has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Connie'. These characteristics in combination distinguish 'Connie' as a new and distinct cultivar:

1. Uniformly mounded plant habit.
2. Daisy spoon-type inflorescences that are about 6.2 cm in diameter.
3. Attractive bi-colored inflorescences with lavender-tipped ray florets that are white at the base.
4. Numerous inflorescences per plant.
5. Excellent garden performance.

The new Chrysanthemum is similar in ray floret color and form to the Chrysanthemum cultivar Naomi (disclosed in U.S. Plant Pat. No. 7,513). However in side-by-side comparisons in Leamington, Ontario, Canada, under commercial practice, plants of the new Chrysanthemum differed from plants of the cultivar Naomi in the following characteristics:

1. Plants of the new Chrysanthemum are shorter and more outwardly spreading than plants of the cultivar Naomi.

2. After pinching, plants of the new Chrysanthemum develop more lateral branches than plants of the cultivar Naomi.
3. The lower leaf lobes of plants of the new Chrysanthemum are shorter than the lower leaf lobes of plants of the cultivar Naomi.
4. Plants of the new Chrysanthemum flower slightly later than plants of the cultivar Naomi.
5. Plants of the new Chrysanthemum have slightly smaller inflorescences than plants of the cultivar Naomi.
6. Ray florets of plants of the new Chrysanthemum are lighter in color than ray florets of plants of the cultivar Naomi. In addition, the base of the ray florets of plants of the new Chrysanthemum have a more pronounced white portion than plants of the cultivar Naomi.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Connie'.

The photograph at the bottom of the sheet comprises a close-up view of typical inflorescences of the cultivar 'Connie'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum production. One unrooted cutting was directly stuck in a 15-cm container and plants were grown in a greenhouse with night interruption lighting for two weeks during late May/early June. At the end of the night interruption lighting period, plants were pinched (terminal apices removed). Three days later, plants were moved into an outdoor production area. Plants flowered about eight weeks later. Measurements and numerical values represent averages for typical flowering containers.

Botanical classification: *Dendranthema grandiflora* cultivar Connie.

Commerical classification: Daisy spoon-type garden chrysanthemum.

Parentage:

*Female or seed parent.*—*Dendranthema grandiflora* cultivar Naomi, disclosed in U.S. Plant Pat. No. 8,988.

*Male or pollen parent.*—Unidentified proprietary seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant descripton:

*Appearance.*—Perennial herbaceous daisy spoon-type garden Chrysanthemum. Inverted triangle. Stems initially upright, then spreading giving a uniformly mounded appearance to the plant. Freely branching; about seven lateral branches develop after removal of terminal apex (pinching). Numerous secondary lateral branches develop at every node.

*Plant height.*—About 28 cm.

*Foliage description.*—Leaf arrangement: Alternate. Length: About 4.75 cm. Width: About 3.75 cm. Apex: Mucronate. Base: Attenuate. Margin: Palmately lobed, sinuses parallel. Texture: Upper and lower surfaces slightly pubescent. Veins prominent on lower surface. Petiole length: About 2 cm. Color: Young foliage upper surface: 147A. Young foliage lower surface: 147B. Mature foliage upper surface: 147A Mature foliage lower surface: 147B. Venation upper surface: 147B. Venation lower surface: 147B.

Inflorescence description:

*Appearance.*—Daisy-type inflorescence form with spoon-shaped ray florets. Inflorescences borne on terminals above foliage, arising from leaf axils. Disk and ray florets arranged acropetally on a capitulum. One inflorescence per terminal with numerous inflorescences per plant.

*Flowering response.*—Under natural conditions, plants flower in the autumn. Plants exposed to 1.5 to 2 weeks of long day/short night conditions after planting followed by short day/long night conditions flower about 55 days later.

*Inflorescence size.*—Diameter: About 6.2 cm. Depth (height): About 1 cm. Diameter of disc: About 1.3 cm.

*Ray florets.*—Shape: Small spoon, straight, very long corolla tube. Length: About 3 cm. Width: At base: About 1.5 cm. At apex: About 3.25 cm. Apex: Spatulate, dentate to rounded. Margin: No margin, fused tube. Texture: Smooth, glabrous. Orientation: Slightly upright, positioned about 120° to the peduncle. Number of ray florets per inflorescence: About 80. Color: When opening: White. Opened inflorescence: Base: White. Apex: 75A to 75C fading to white towards base.

*Disc florets.*—Shape: Enlarged tubular, apex dentate. Length: About 7 mm. Width: Apex: About 1.5 mm. Base: About 1 mm. Number of disc florets per inflorescence: Numerous. Color: Immature: 154A to 5A. Mature: Apex: 14A. Mid-section: Light green. Base: White.

*Peduncle.*—Aspect: Flexible, angled about 40° to the stem. Length: First peduncle: About 5.75 cm. Fourth peduncle: About 8.5 cm. Texture: Pubescent. Color: 143A.

*Reproductive organs.*—Androecium: Present on disc florets only. Anther color: 14A. Pollen: Amount: Low. Color: 17A. Gynoecium: Present on both ray and disc florets.

Disease resistance: No known Chrysanthemum diseases observed to date on plants grown under commercial production conditions.

Seed production: Seed production has not been observed.

It is claimed:

1. A new and distinct cultivar of Chrysanthemum plant named 'Connie', as illustrated and described.

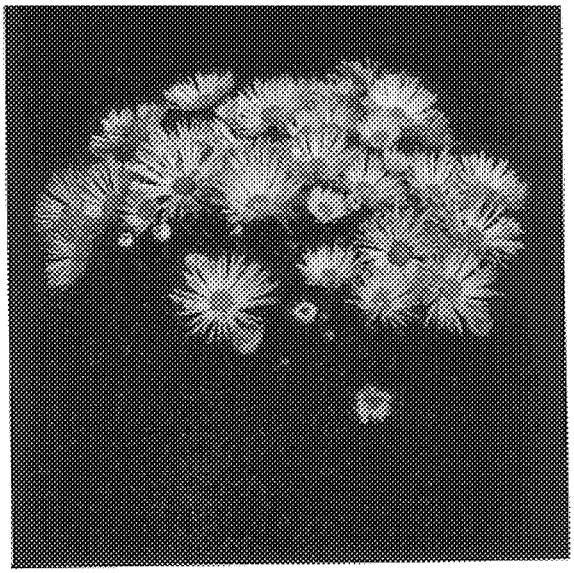
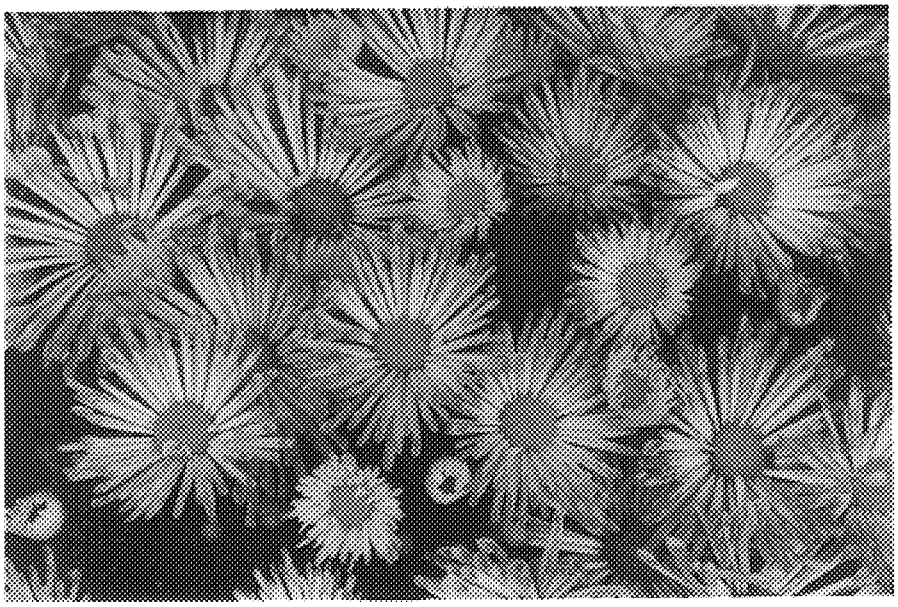

* * * * *